US012168695B2

(12) United States Patent
Soliman

(10) Patent No.: US 12,168,695 B2
(45) Date of Patent: *Dec. 17, 2024

(54) BISPECIFIC ANTIBODY FOR CANCER IMMUNOTHERAPY

(71) Applicant: H. LEE MOFFITT CANCER CENTER AND RESEARCH INSTITUTE, INC., Tampa, FL (US)

(72) Inventor: Hatem Soliman, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 306 days.

This patent is subject to a terminal disclaimer.

(21) Appl. No.: 17/810,447

(22) Filed: Jul. 1, 2022

(65) Prior Publication Data
US 2022/0380481 A1   Dec. 1, 2022

Related U.S. Application Data

(63) Continuation of application No. 16/058,398, filed on Aug. 8, 2018, now Pat. No. 11,396,554, which is a continuation of application No. 15/120,033, filed as application No. PCT/US2015/061566 on Nov. 19, 2015, now abandoned.

(60) Provisional application No. 62/088,577, filed on Dec. 6, 2014.

(51) Int. Cl.
C07K 16/30 (2006.01)
C07K 16/28 (2006.01)
C07K 16/46 (2006.01)

(52) U.S. Cl.
CPC .......... C07K 16/30 (2013.01); C07K 16/2809 (2013.01); C07K 16/468 (2013.01); C07K 2317/31 (2013.01); C07K 2317/56 (2013.01); C07K 2317/565 (2013.01); C07K 2317/622 (2013.01)

(58) Field of Classification Search
CPC .............. C07K 16/2089; C07K 16/486; C07K 2317/31
USPC ..................................................... 424/136.1
See application file for complete search history.

(56) References Cited

U.S. PATENT DOCUMENTS

| | | | |
|---|---|---|---|
| 5,579,250 A | 11/1996 | Balaji et al. | |
| 5,612,895 A | 3/1997 | Balaji et al. | |
| 5,631,280 A | 5/1997 | Ciccarone et al. | |
| 6,440,735 B1 | 8/2002 | Gaeta et al. | |
| 6,713,055 B2 | 3/2004 | Schiff et al. | |
| 8,008,449 B2 | 8/2011 | Selby et al. | |
| 8,552,154 B2 | 10/2013 | Freeman | |
| 8,617,546 B2 | 12/2013 | Kang et al. | |
| 8,748,356 B2 | 6/2014 | Raghunathan et al. | |
| 11,155,634 B2 | 10/2021 | Soliman | |
| 11,224,663 B2 * | 1/2022 | Cuevas Marchante ..................... C07D 309/30 |
| 11,396,554 B2 * | 7/2022 | Soliman ............... C07K 16/468 |
| 2004/0038339 A1 | 2/2004 | Kufer et al. | |
| 2005/0079184 A1 | 4/2005 | Hising-Chang et al. | |
| 2005/0136050 A1 | 6/2005 | Kufer et al. | |
| 2006/0233787 A1 | 10/2006 | Le Gall et al. | |
| 2008/0213256 A1 | 9/2008 | Kufer et al. | |
| 2014/0088295 A1 | 3/2014 | Smith et al. | |
| 2014/0099318 A1 | 4/2014 | Huang | |
| 2017/0218081 A1 | 8/2017 | Magliery | |
| 2019/0276555 A1 | 9/2019 | Solimam | |
| 2019/0315882 A1 | 10/2019 | Soliman | |

FOREIGN PATENT DOCUMENTS

WO 9957150 A2 11/1999

OTHER PUBLICATIONS

Weißmüller et al (PLoS One. 2016; 11(3): e0149093 (Published online Mar. 9, 2016)).*
Lutterbuese, R. et al., Proc. Natl. Acad. Sci. USA 107, 12605-12610 (2010)).*
Xiang et al (Mol Biother Mar. 1992;4(1):15-23); Abstract).*
Hombach et al Anticancer Res ) May-Jun. 1997;17(3C):2025-32).*
Nicolet, C.M., et al., "TAG-72 reactive antibody CC49 recognizes molecules expressed by hematopoietic cell lines", Tumour Biol., vol. 18 (1997), pp. 356-366.
Lutterbuese, R., et al., "T cell-engaging BiTE antibodies specific for EGFR potently eliminate KRAS- and BRAF-mutated colorectal cancer cells", Proc. Natl. Acad. Sci. USA, vol. I 107 (2010), pp. 12605-12610.
ATCC MCF-7Tam (data sheet pp. 1-8 (Aug. 30, 2021)).
ATCC BT-474 (data sheet pp. 1-9 (Aug. 30, 2021)).
ATCC NIH-OVCAR-3 (data sheet pp. 1-9 (Aug. 30, 2021)).
Pavlinkova, et al., "?", The Journal of Nuclear Medicine, vol. 40, No. 9 (1999), pp. 1536-1546.
Albrecht, et al., "Monospecific bivalent scFv-SH: Effects of linker length and location of an engineered cysteine on production, antigen binding activity and free SH accessibility," Journal of Immunological Methods 310, Issues 1-2, (2006), pp. 100-116.
Argos, et al., "An investigation of oligopeptides linking domans in protein tertiary structures and possible candidates for general gene fusion," J. Mol. Biol., vol. 211, No. 4 (1990), pp. 943-958.
Bird, et al., "Single-chain antigen-binding proteins," Science, vol. 242 (1988), pp. 423-426.
Feng, et al., "Design and assembly of anti-CD16 ScFv antibody with two different linker peptides," J. Immunol. Methods, vol. 282, No. 1-2 (2003), pp. 33-43.

(Continued)

Primary Examiner — Lynn A Bristol
(74) Attorney, Agent, or Firm — Thomas | Horstemeyer, LLP

(57) ABSTRACT

Disclosed are compositions and methods for targeted treatment of TAG-72-expressing cancers. In particular, bispecific antibodies are disclosed that are able to engage T-cells to destroy TAG-72-expressing malignant cells.

6 Claims, 9 Drawing Sheets
Specification includes a Sequence Listing.

(56) References Cited

OTHER PUBLICATIONS

Griffiths, et al., "Strategies for selection of antibodies by phage display," Curr Opin Biotechnol., vol. 9, No. 1 (1998), pp. 102-108.
Holliger, "Engineered antibody fragments and the rise of single domans," Nature Biotechnology, vol. 23 (2005), pp. 1126-1136.
Huston, et al., "[3]Protein engineering of single-chain Fv analogs and fusion proteins," Methods Enzymol., vol. 203 (1991), pp. 46-88.
Kumada, "Polypeptide linkers suitable for the efficient production of dimeric scFv in *Escherichia coli*," Biochemical Engineering Journal, vol. 35, No. 2 (Year?), pp. 158-165.
International Search Report and Written Opinion, PCT Patent Application No. PCT/US2015/61566, mailed Feb. 9, 2016.
Smallshaw, et al., "Synthesis, cloning and expression of the single-chain Fv gene of the HPr-specific monoclonal antibody, Je142. Determination of binding constants with wild-type and mutant HPrs," Protein Eng., vol. 12, No. 7 (1999), pp. 623-630.
Takkinen, et al., "An active single-chain antibody containing a cellulase linker domain in secreted by Escherichia coli," Protein Eng., vol. 4, No. 7 (1991), pp. 837-841.
Whitlow, et al., "An improved linker for single-chain Fv with reduced aggregation and enhanced proteolytic stability," Protein Eng., vol. 6, No. 8 (1993), pp. 989-995.

\* cited by examiner

BISPECIFIC ANTIBODY FOR CANCER IMMUNOTHERAPY

CROSS-REFERENCE TO RELATED APPLICATIONS

This application is a continuation of U.S. patent application Ser. No. 16/058,398, filed Aug. 8, 2018, which is a continuation of U.S. patent application Ser. No. 15/120,033, which is a national stage application, filed under 35 U.S.C. § 371, of International Patent Application No. PCT/US15/61566, filed on Nov. 19, 2015, which claims benefit of U.S. Provisional Application No. 62/088,577, filed Dec. 6, 2014, which are hereby incorporated herein by reference in their entireties.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Disclosed are bispecific antibodies that are able to engage T-cells to destroy TAG-72-expressing malignant cells. The antibodies can be engineered from fusion polypeptides comprising 1) variable domains of antibodies that specifically bind an immune cell antigen and 2) variable domains of antibodies that specifically bind TAG-72. In some embodiments, the antibody is a diabody (fusion polypeptide) having, for example, the following formula:

$V_L$-$V_H$T & $V_L$T-$V_H$I, or $V_H$I-$V_L$T & $V_H$T-$V_L$I, wherein "$V_H$I" is a light chain variable domain specific for an immune cell antigen;
wherein "$V_H$T" is a heavy chain variable domain specific for TAG-72;
wherein "$V_L$T" is a light chain variable domain specific for TAG-72;
wherein "$V_H$I" is a heavy chain variable domain specific for the immune cell antigen; and
wherein "-" consists of a peptide linker or a peptide bond.

In some embodiments, the antibody is a Bispecific T-Cell Engaging (BITE) antibody (fusion polypeptide) having, for example, the following formula:

$V_L$I-$V_H$I-$V_L$T-$V_H$T, $V_H$I-$V_L$I-$V_H$T-$V_L$T, $V_L$I-$V_H$I--$V_H$T-$V_L$T, or $V_H$I-$V_L$I-$V_L$T-$V_H$T, wherein "$V_L$I" is a light chain variable domain specific for an immune cell antigen;
wherein "$V_H$T" is a heavy chain variable domain specific for TAG-72;
wherein "$V_L$T" is a light chain variable domain specific for TAG-72;
wherein "$V_H$I" is a heavy chain variable domain specific for the immune cell antigen;
wherein "-" consists of a peptide linker or a peptide bond; and
wherein "--" consists of a peptide linker or a peptide bond.

The immune cell antigen can be a cell surface molecule that is expressed on human NK cells, T cells, monocytes, macrophages or granulocytes. For example, the cell surface molecule can be antigen CD2, CD3, CD16, CD64, CD89; NKp30, NKp44, NKp46, NKp80 (KLR-F1), NKG2C or NKG2D.

Also disclosed is an isolated nucleic acid encoding the disclosed fusion polypeptide, as well as nucleic acid vectors containing this isolated nucleic acid operably linked to an expression control sequence. Also disclosed are cells transfected with these vectors and the use of these cells to produce the disclosed fusion polypeptides.

A bi-specific antigen binding molecule can be formed from dimerization of heavy and light chains. In these embodiments, the $V_L$I dimerizes with $V_H$I to form an antigen binding site for an immune cell antigen (e.g., CD3) and the $V_H$T dimerizes with $V_L$T to form an antigen binding site for TAG-72.

Also disclosed is a bispecific antibody that is a single polypeptide chain comprising a bispecific antibody having a first antigen-binding region and a second antigen-binding region. In some cases, the first antigen-binding region is capable of recruiting the activity of a human immune effector cell by specifically binding to an immune cell antigen located on the human immune effector cell; and the second antigen-binding region is capable of specifically binding to TAG-72 on a target cell.

Each of the first and second portions can comprise 1, 2, 3, or more antibody variable domains. In particular embodiments, each of the first and second portions contains two variable domains, a variable heavy ($V_H$) domain and a variable light ($V_L$) domain.

In some cases, the bispecific antibody has an affinity for TAG-72 corresponding to a $K_D$ of about $10^{-7}$ M, $10^{-8}$ M, $10^{-9}$ M, or less.

Each of the first and second portions can be derived from natural antibodies, such as monoclonal antibodies. In some cases, the antibody is human. In some cases, the bispecific antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Currently, the most widely used technique for antibody human adaptation is known as "CDR grafting." The scientific basis of this technology is that the binding specificity of an antibody resides primarily within the three hypervariable loops known as the complementarity determining regions (CDRs) of its light and heavy chain variable regions (V-regions), whereas the more conserved framework regions (framework, FW; framework region, FR) provide structure support function. By grafting the CDRs to an appropriately selected FW, some or all of the antibody-binding activity can be transferred to the resulting recombinant antibody.

CDR grafting is the selection of a most appropriate human antibody acceptor for the graft. Various strategies have been developed to select human antibody acceptors with the highest similarities to the amino acid sequences of donor CDRs or donor FW, or to the donor structures. All these "best fit" strategies, while appearing very rational, are in fact based on one assumption, i.e., a resulting recombinant antibody that is most similar (in amino acid sequence or in structure) to the original antibody will best preserve the original antigen binding activity.

Not all amino acids in the CDRs are involved in antigen binding. Thus, it has been proposed that the grafting of only those residues that are critical in antigen-antibody interaction—the so-called specificity determining residues grafting (SDR-grafting)—will further increase the content of human antibody sequences in the resulting recombinant antibody. The application of this strategy requires information on the antibody structure as well as antibody-antigen contact residues, which are quite often unavailable. Even when such information is available, there is no systematic method to reliably identify the SDRs, and SDR-grafting remains so far mostly at the basic research level.

Recently, a strategy called "human framework shuffling" has been developed. This technique works by ligating DNA fragments encoding CDRs to DNA fragments encoding human FR1, FR2, FR3, and FR4, thus generating a library of all combinations between donor CDRs and human FRs. Methods for making human-adapted antibodies based on molecular structures, modeling and sequences for human engineering of antibody molecules are disclosed in U.S. Pat. No. 8,748,356, which is incorporated by reference for these methods.

The effector cell recruited by the bispecific antibody is one capable of exerting a cytotoxic or an apoptotic effect on a target cell. In some embodiments, the human effector cell can in some embodiments be a member of the human lymphoid lineage or myeloid lineage. As an example, for lymphoid cells, the immune cell antigen can be selected from the group consisting of human CD3 antigen, human CD16 antigen, human NKG2D antigen, human CD2 antigen, human CD28 antigen, and human CD25 antigen. Similarly, for myeloid cells, the immune cell antigen can be human CD64 antigen or human CD89 antigen.

Also disclosed is a pharmaceutical composition comprising a molecule disclosed herein in a pharmaceutically acceptable carrier. Also disclosed is a method for treating cancer in a subject that involves administering to the subject a therapeutically effective amount of a disclosed pharmaceutical composition. Also disclosed is a kit comprising a bispecific antibody disclosed herein.

Also disclosed is an expression vector comprising an isolated nucleic acid encoding a bispecific antibody disclosed herein operably linked to an expression control sequence. Also disclosed is a cell comprising the disclosed expression vector. The cell can be a primary cell, transformed cell, cell line, or the like. In some cases, the cell is a mammalian cell line. In some cases, the cell is a non-mammalian cell line. For example, the cell can be a bacteria or insect cell line.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
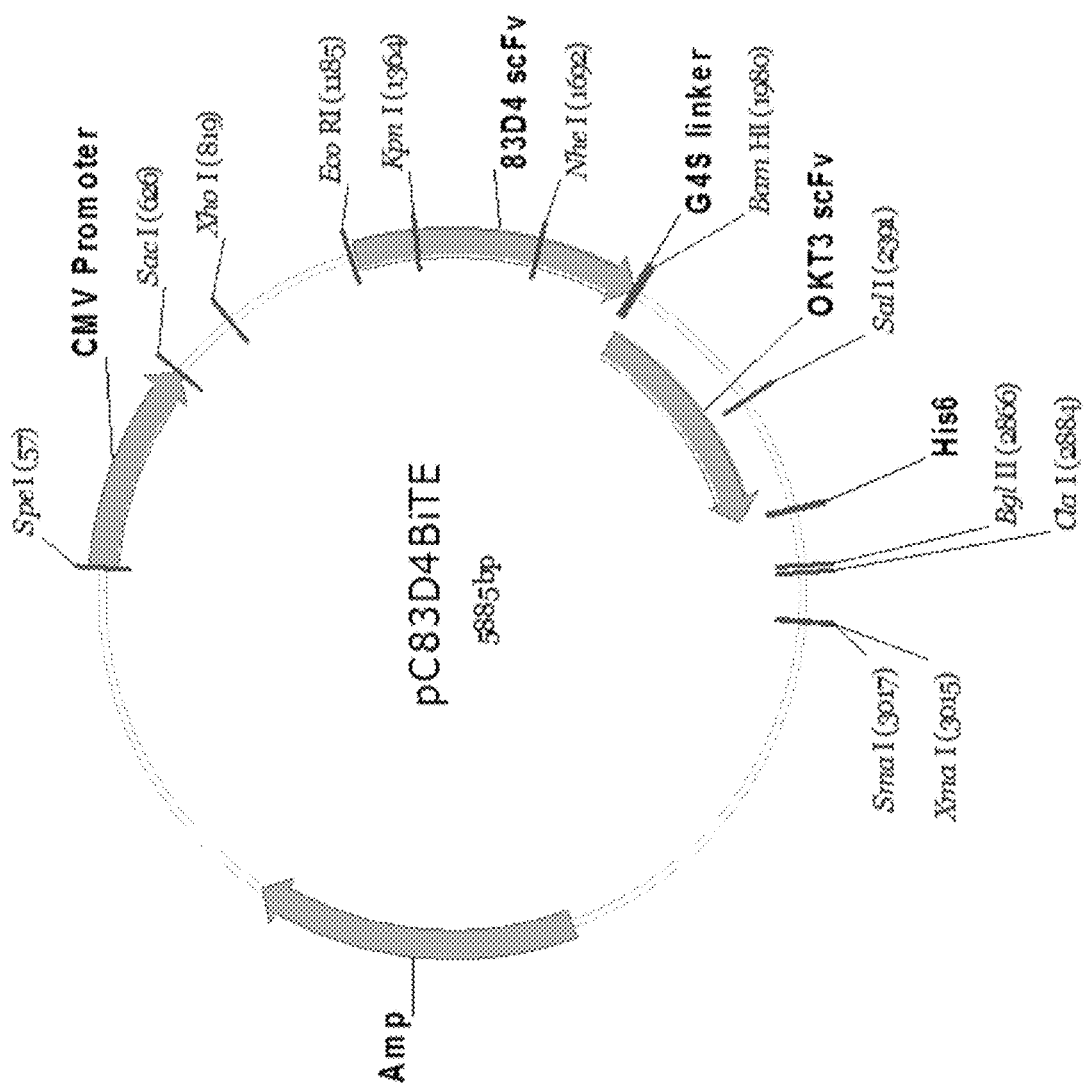
FIG. 1 is a map of a plasmid for 83D4 BITE antibody.

Many different cancers express abnormal cell surface markers and these markers can be used to identify and target them while sparing normal tissues. One of these markers is TAG-72, which is also known by the name Sialyl Tn. This glycoprotein is considered a pan-carcinoma marker that is widely expressed in numerous solid tumors including breast and gynecologic cancers. This target is used herein to make the cancer cells more susceptible to immune attack via a bispecific antibody, such as a bispecific T cell engager (BITE) antibody. These antibodies have binding activity against two different targets, with one of the targets being an immune cell receptor, such as the CD3 receptor present on killer T immune cells. The concept is that the BITE antibody will activate the killer T cell once it binds to the CD3, while the other end of the antibody binds TAG-72 on the surface of the cancer cells. The activated T cell will be held in close proximity to the cancer cell and start to kill the cancer cell through an immune mediated attack. A bispecific antibody is disclosed that can be used in immunotherapy approaches against TAG-72 expressing tumor cells.

Disclosed are compositions and methods for targeted treatment of TAG-72-expressing cancers. In particular, bi-specific T-cell engagers (BiTEs) are disclosed that are able to direct cytotoxic T-cells to TAG-72-expressing cancers.

Provided are fusion polypeptides capable of forming a bispecific engineered antibody that is able to engage T-cells to destroy TAG-72 expressing malignant cells. The engineered antibody may comprise for example, at least one scFv, at least one Fab fragment, at least one Fv fragment, etc. It may be bivalent, trivalent, tetravalent, etc. The multivalent antibodies is multispecific, e.g., bispecific, trispecific, tetraspecific, etc. The multivalent antibodies may be in any form, such as a diabody, triabody, tetrabody, etc.

Bispecific Antibodies

Bispecific antibodies may contain a heavy chain comprising one or more variable regions and/or a light chain comprising one or more variable regions. Bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular VH-VL pairings with formation of a 60 kDa non-covalent scFv dimer "diabody". The diabody format can also be used for generation of recombinant bis-specific antibodies, which are obtained by the noncovalent association of two single-chain fusion products, consisting of the VH domain from one antibody connected by a short linker to the VL domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein.

Peptide linkers (-) suitable for production of scFv antibodies are described in Kumada Y, et al. Biochemical Engineering Journal. 2007 35 (2): 158-165; Albrecht H, et al. J Immunol Methods. 2006 310 (1-2): 100-16; Feng J, et al. J Immunol Methods. 2003 282 (1-2): 33-43; Griffiths A D, et al. Curr Opin Biotechnol. 1998 9 (1): 102-8; Huston J S, et al. Methods Enzymol. 1991 203:46-88; Bird R E, et al. Science. 1988 242 (4877): 423-6; Takkinen K, et al. Protein Eng. 1991 4 (7): 837-41; Smallshaw J E, et al. Protein Eng. 1999 12 (7): 623-30; Argos P. J Mol Biol. 1990 211 (4): 943-58; and Whitlow M, et al. Protein Eng. 1993 6 (8): 989-95, which are hereby incorporated by reference for the teachings of these linkers and methods of producing scFv antibodies against different targets using various linkers.

Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest (e.g., TAG-72). The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

In some cases, the $V_H T$ comprises the amino acid sequence SEQ ID NO:2, or a fragment or variant thereof able to bind TAG-72. In some cases, the $V_L T$ comprises the amino acid sequence SEQ ID NO:4, or a fragment or variant thereof able to bind TAG-72.

The affinity/specificity of the binding construct is driven in large part by specific sequences within complementarity determining regions (CDRs) in the heavy and light chain. Each $V_H$ and $V_L$ sequence will have three CDRs (CDR1, CDR2, CDR3). In some embodiments, the $V_H T$ comprises an amino acid sequence variant of SEQ ID NO:2 comprising at least the following CDR domains: CDR1: DHAIH (SEQ ID NO: 12), CDR2: WIGYFSPGNDDFKYNERFKG (SEQ ID NO: 13), and CDR3: LNMAY (SEQ ID NO:14). In some cases, the second antigen-binding region comprises a $V_H$ domain having the amino acid sequence of SEQ ID NO: 2. In some embodiments, the $V_L T$ comprises an amino acid sequence variant of SEQ ID NO:2 comprising at least the following CDR domains: CDR1: KSSQSLLYSGNQK-NYLA (SEQ ID NO:15), CDR2: WASARES (SEQ ID NO:16), and CDR3: QQYYSYPLT (SEQ ID NO:17). In some cases, the second antigen-binding region comprises a $V_L$ domain having the amino acid sequence of SEQ ID NO:4.

The particular length of the peptide linker (--) used to join the scFv molecules together is important in determining half-life, immunogenicity, and activity of the overall construct. In some embodiments, the linker sequence (--) is 4, 5, 6, 7, 8, 9, 10, 11, 12, 13, 14, 15, 16, 17, 18, 19, 20, 21, 22, 23, 24, 25 or more amino acids in length. In some embodiments, the linker sequence (--) comprises GGGGS (SEQ ID NO: 18). In some cases, the linker comprises 2, 3, 4, 5, or more GGGGS sequences. The linker is preferably long enough to not interfere with proper folding and association of the $V_H$-$V_L$ chains but not so long as to cause added immunogenicity.

Most variations occur in the CDR3 regions therefore it is predicted that much of the specificity is dictated by sequence changes in these regions. Affinity maturation using site directed mutagenesis and phage library experiments can be used to determine high affinity TAG72 sequences. This would focus on mutations in these key regions (particularly CDR3). In some cases, the $V_H T$ and $V_L T$ sequences comprise one or more amino acid substitutions within the above described CDR1, CDR2, and/or CDR3 sequences, including 1, 2, or 3 amino acid substitutions. These substitutions can be assayed using routine immunoassay techniques to evaluate changes in affinity for TAG-72.

In some cases, the $V_H I$-$V_L I$ scFv sequence comprises the amino acid sequence DIKLQQSGAELARP-GASVKMSCKTSGYTFTRYTMHWKQRPGQGLEWI-GYINPSR GYTNYNQKFKDKATLTTDKSSSTAYMQLSSLTSED-SAVYYCARYYDDHYCLDYWG QGTTLTVSSVEG-GSGGSGGSGGSGGVDDIQLTQSPAIM-SASPGEKVTMTCRASSS VSYMNWYQQKSGTSPKRWIYDTSK-VASGVPYRFSGSGSGTSYSLTISSM EAE-DAATYYCQQWSSNPLTFGAGTKLELKHHHHHH (SEQ ID NO: 19, OKT3-H6), or a fragment or variant thereof able to bind CD-3. This is a commonly used sequence of T cell activating antibodies which work through binding of a set of narrow sequences on the CD3 epsilon subunit (AAs 34, 46, 48, and 79-85). The poly histidine tag at the end of the sequence allows for purification of the artificial construct and use of his tagged fluorescence antibodies for detection.

In particular cases, the antibody has a sequence as set out in SEQ ID NO: 11.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

In some embodiments, the bispecific antibody may be subjected to an alteration to render it less immunogenic when administered to a human. Such an alteration may comprise one or more of the techniques commonly known as chimerization, humanization, CDR-grafting, deimmunization and/or mutation of framework region amino acids to correspond to the closest human germline sequence (germlining). Bispecific antibodies which have been altered will therefore remain administrable for a longer period of time with reduced or no immune response-related side effects than corresponding bispecific antibodies which have not undergone any such alteration(s). One of ordinary skill in the art will understand how to determine whether, and to what degree an antibody must be altered in order to prevent it from eliciting an unwanted host immune response.

Pharmaceutical Composition

Also disclosed is a pharmaceutical composition comprising a disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, PA. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutically acceptable carriers include any and all suitable solvents, dispersion media, coatings, antibacterial and antifungal agents, isotonicity agents, antioxidants and absorption delaying agents, and the like that are physiologically compatible with a bispecific antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical bispecific antibodies may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical bispecific antibodies may also comprise isotonicity agents, such as sugars, polyalcohols, such as mannitol, sorbitol, glycerol or sodium chloride in the compositions.

The pharmaceutical bispecific antibodies may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The bispecific antibodies may be prepared with carriers that will protect the bispecific antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Also disclosed is the use of a disclosed bispecific antibody for use as a medicament for the treatment of various forms of cancer, including metastatic cancer and refractory cancer.

Methods of Treatment

Also disclosed is a method for treating a TAG-72-expressing cancer in a subject by administering to the subject a therapeutically effective amount of the disclosed pharmaceutical composition. The method can further involve administering to the subject lenalidomide, or an analogue or derivative thereof.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a TAG-72-expressing cancer. Thus, the method can further comprise identifying a subject at risk for a TAG-72-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The cancer of the disclosed methods can be any TAG-72-expressing cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

A bispecific antibody may also be administered prophylactically in order to reduce the risk of developing cancer, delay the onset of the occurrence of an event in cancer progression, and/or reduce the risk of recurrence when a cancer is in remission.

The disclosed bispecific antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic, or anti-angiogenic agent.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

In some embodiments, a therapeutic agent for use in combination with a bispecific antibody for treating the disorders as described above may be an anti-cancer immunogen, such as a cancer antigen/tumor-associated antigen (e.g., epithelial cell adhesion molecule (EpCAM/TAC-STDI), mucin 1 (MUC1), carcinoembryonic antigen (CEA), tumor-associated glycoprotein 72 (TAG-72), gplOO, Melan-A, MART-1, KDR, RCASI, MDA7, cancer-associated viral vaccines (e.g., human papillomavirus vaccines) or tumor-derived heat shock proteins.

In some embodiments, a therapeutic agent for use in combination with a bispecific antibody for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L. Flt3 ligand, stem cell factor, ancestim, and TNFa. Suitable chemokines may include Glu-Leu-Arg (ELR)-negative chemokines such as IP-10, MCP-3, MIG, and SDF-Ia from the human CXC and C-C chemokine families. Suitable cytokines include cytokine derivatives, cytokine variants, cytokine fragments, and cytokine fusion proteins.

In some embodiments, a therapeutic agent for use in combination with a bispecific antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a bispecific antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with a bispecific antibody for treating the disorders as described above may be an anti-anergic agent, such as molecules that block the activity of CTLA-4, e.g. ipilimumab.

In some embodiments, a therapeutic agent for use in combination with a bispecific antibody for treating the disorders as described above may be an anti-cancer nucleic acid or an anti-cancer inhibitory RNA molecule.

In some embodiments, the bispecific antibody is for use in combination with one or more other therapeutic antibodies, such as ofatumumab, zanolimumab, daratumumab, ranibizumab, nimotuzumab, panitumumab, hu806, daclizumab, basiliximab, infliximab, adalimumab, natalizumab, omalizumab, efalizumab, and/or rituximab.

Combined administration, as described above, may be simultaneous, separate, or sequential. For simultaneous administration the agents may be administered as one composition or as separate compositions, as appropriate.

In some embodiments, the disclosed bispecific is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed bispecific antibody is administered in combination with surgery.

Definitions

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "bispecific antibody" refers to an antibody having two different antigen-binding regions defined by different antibody sequences. This can be understood as different target binding but includes as well binding to different epitopes in one target.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "protein" (if single-chain), "polypeptide" and "peptide" are used interchangeably herein when referring to a gene product, e.g., as may be encoded by a coding sequence. When referring to "polypeptide" herein, a person of skill in the art will recognize that a protein can be used instead, unless the context clearly indicates otherwise. A "protein" may also refer to an association of one or more polypeptides. By "gene product" is meant a molecule that is produced as a result of transcription of a gene. Gene products include RNA molecules transcribed from a gene, as well as proteins translated from such transcripts.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described.

Nevertheless, it will be understood that various modifications may be made without departing from the spirit and scope of the invention. Accordingly, other embodiments are within the scope of the following claims.

EXAMPLES

Example 1: Bispecific Tandem Antibody for Cancer Immunotherapy

Materials and Methods

A tandem BITE antibody was produced using a proprietary linker to enhance half-life of the antibody and minimize immunogenicity of the BITE protein. The initial TAG-72 binding candidate focused on a sequence known as 83D4. The CD3 binding clone used is a well characterized OKT3 binding antibody (FIG. 1).

CC49_VH (GenBank accession: L14553)

(SEQ ID NO: 1)
caggttcagttgcagcagtctgacgctgagttggtgaaacctggggcttc agtgaagatttcctgcaaggcttctggctacaccttcactgaccatgcaa ttcactgggtgaaacagaaccctgaacagggcctggaatggattggatat ttttctcccggaaatgatgattttaaatacaatgagaggttcaagggcaa ggccacactgactgcagacaaatcctccagcactgcctacgtgcagctca acagcctgacatctgaggattctgcagtgtatttctgtacaagatccctg aatatggcctactggggtcaaggaacctcagtcaccgtctcctca.

(SEQ ID NO: 2)
QVQLQQSDAELVKPGASVKISCKASGYTFTDHAIHWVKQNPEQGLEWIGY

FSPGNDDFKYNERFKGKATLTADKSSSTAYVQLNSLTSEDSAVYFCTRSL

NMAYWGQGTSVTVSS.

CC49_VL (GenBank accession: L14553)

(SEQ ID NO: 3)
gacattgtgatgtcacagtctccatcctccctacctgtgtcagttggcga gaaggttactttgagctgcaagtccagtcagagccttttatatagtggta atcaaaagaactacttggcctggtaccagcagaaaccagggcagtctcct aaactgctgatttactgggcatccgctagggaatctggggtccctgatcg

```
cttcacaggcagtggatctgggacagatttcactctctccatcagcagtg tgaagactgaagacctggcagtttattactgtcagcagtattatagctat cccctcacgttcggtgctgggaccaagctggtgctgaaa.
```

```
                                       (SEQ ID NO: 4)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLK.
``` nter_scFv_linker
```
                                       (SEQ ID NO: 5)
LSADDAKKDAAKKDDAKKDDAKKDL
```

CC49_scFv_1 (VH-linker-VL)
```
                                       (SEQ ID NO: 6)
QVQLQQSDAELVKPGASVKISCKASGYTFTDHAIHWVKQNPEQGLEWIGY

FSPGNDDFKYNERFKGKATLTADKSSSTAYVQLNSLTSEDSAVYFCTRSL

NMAYWGQGTSVTVSSLSADDAKKDAAKKDDAKKDDAKKDLDIVMSQSPSS

LPVSVGEKVTLSCKSSQSLLYSGNQKNYLAWYQQKPGQSPKLLIYWASAR

ESGVPDRFTGSGSGTDFTLSISSVKTEDLAVYYCQQYYSYPLTFGAGTKL

VLK.
```

CC49_scFv_2 (VL-linker-VH)
```
                                       (SEQ ID NO: 7)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFKYNE

RFKGKATLTADKSSSTAYVQLNSLTSEDSAVYFCTRSLNMAYWGQGTSVT

VSS.
``` linker_OKT3_scFv_H6
```
                                       (SEQ ID NO: 8)
ggggggggggggatccgatatcaaactgcagcagagcggagccgaactggc aagacccggagcaagcgtcaaaatgtcatgtaaaacctcagggtacacat tcactaggtataccatgcactgggtgaaacagcgaccaggacagggtctg gagtggatcggatatattaaccctcccgagggtacacaaactacaacca gaagtttaaagacaaggccacactgaccaccgataagtccagctctactg cttacatgcagctgagttcactgaccagcgaggactctgctgtgtactat tgcgcaaggtactatgacgatcattactgtctggattattggggccaggg aactaccctgactgtgtccagcgtcgaaggcggaagtgggggttcaggcg gaagcggggttctggcggagtcgacgatatccagctgacccagagcccc gcaattatgtcagcctcccctggcgaaaaagtgaccatgacatgcagagc ctctagttcagtctcctacatgaattggtatcagcagaaaagtggaacaa gccctaagagatggatctacgacacttctaaggtggcatccggcgtccca tatcgcttcagcgggtctggtagtggcacttcatactccctgaccatttc cagcatggaggctgaagatgccgctacatactattgtcagcagtggtcta gtaaccctctgacctttggggctggaactaaactggaactgaagcatcat catcatcatcac.
```

```
                                       (SEQ ID NO: 9)
GGGGSDIKLQQSGAELARPGASVKMSCKTSGYTFTRYTMHWVKQRPGQGL

EWIGYINPSRGYTNYNQKFKDKATLTTDKSSSTAYMQLSSLTSEDSAVYY

CARYYDDHYCLDYWGQGTTLTVSSVEGGSGGSGGSGGSGGVDDIQLTQSP

AIMSASPGEKVTMTCRASSSVSYMNWYQQKSGTSPKRWIYDTSKVASGVP

YRFSGSGSGTSYSLTISSMEAEDAATYYCQQWSSNPLTFGAGTKLELKHH

HHHH.
```

CC49_BITE_1: CC49_SCFV-1-LINKER-OKT3_SCFV-H6
```
                                       (SEQ ID NO: 10)
QVQLQQSDAELVKPGASVKISCKASGYTFTDHAIHWVKQNPEQGLEWIGY

FSPGNDDFKYNERFKGKATLTADKSSSTAYVQLNSLTSEDSAVYFCTRSL

NMAYWGQGTSVTVSSLSADDAKKDAAKKDDAKKDDAKKDLDIVMSQSPSS

LPVSVGEKVTLSCKSSQSLLYSGNQKNYLAWYQQKPGQSPKLLIYWASAR

ESGVPDRFTGSGSGTDFTLSISSVKTEDLAVYYCQQYYSYPLTFGAGTKL

VLKGGGGSDIKLQQSGAELARPGASVKMSCKTSGYTFTRYTMHWKQRPGQ

GLEWGYINPSRGYTNYNQKFKDKATLTTDKSSSTAYMQLSSLTSEDSAVY

YCARYYDDHYCLDYWGQGTTLTVSSVEGGSGGSGGSGGSGGVDDIQLTQS

PAIMSASPGEKVTMTCRASSSVSYMNWYQQKSGTSPKRWIYDTSKVASGV

PYRFSGSGSGTSYSLTISSMEAEDAATYYCQQWSSNPLTFGAGTKLELKH

HHHHH.
```

CC49_BITE_2: CC49_SCFV-2-LINKER-OKT3_SCFV-H6
```
                                       (SEQ ID NO: 11)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFKYNE

RFKGKATLTADKSSSTAYVQLNSLTSEDSAVYFCTRSLNMAYWGQGTSVT

VSSGGGGSDIKLQQSGAELARPGASVKMSCKTSGYTFTRYTMHWVKQRPG

QGLEWIGYINPSRGYTNYNQKFKDKATLTTDKSSSTAYMQLSSLTSEDSA

VYYCARYYDDHYCLDYWGQGTTLTVSSVEGGSGGSGGSGGSGGVDDIQLT

QSPAIMSASPGEKVTMTCRASSSVSYMNWYQQKSGTSPKRWIYDTSKVAS

GVPYRFSGSGSGTSYSLTISSMEAEDAATYYCQQWSSNPLTFGAGTKLEL

KHHHHHH.
```

Results

Figure 2A:
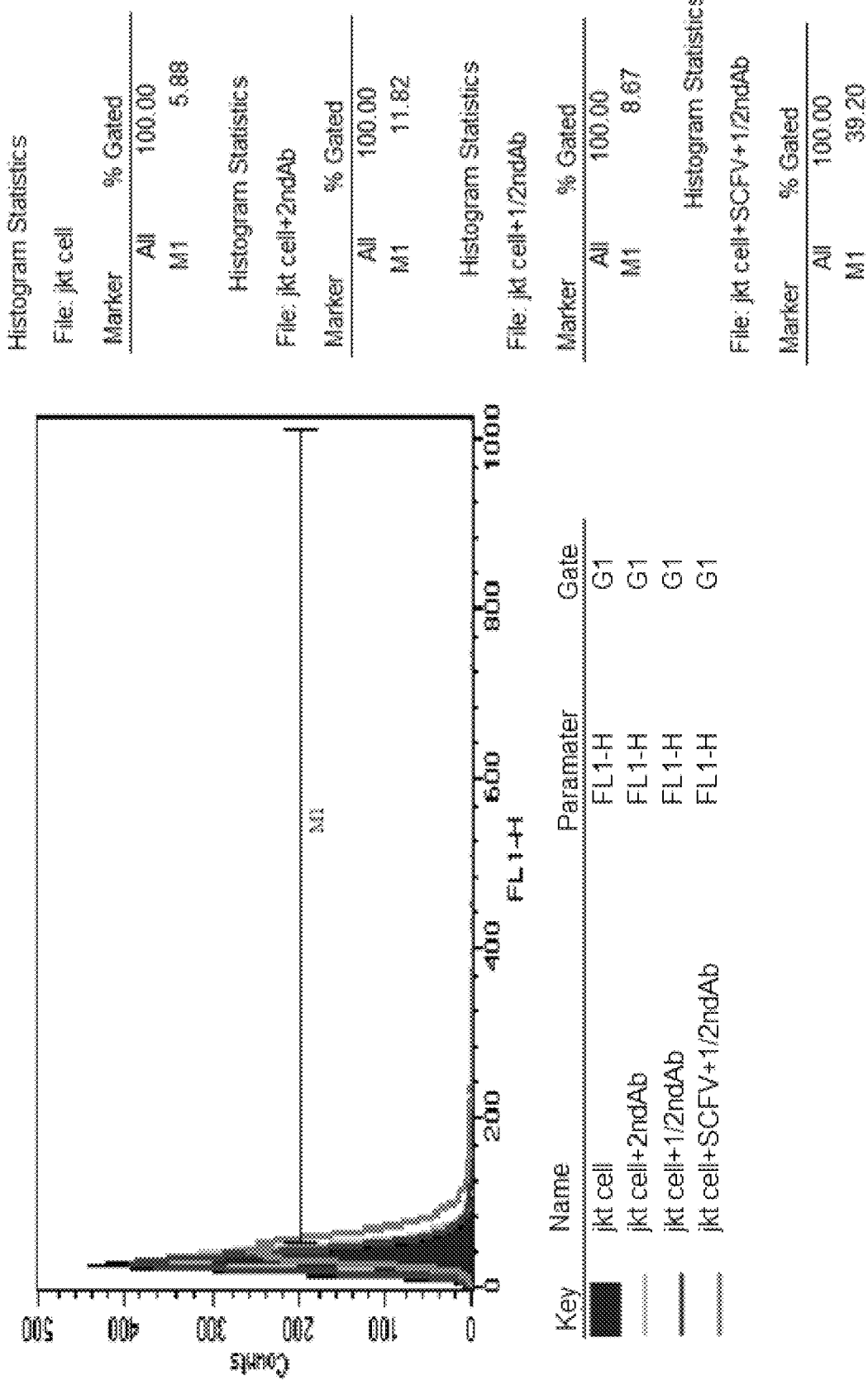
FIGS. 2A and 2B show flow cytometry binding of 83D4 BITE antibody to jurkat (FIG. 2A) and MCF-7 (FIG. 2B) cell lines.
Figure 2B:
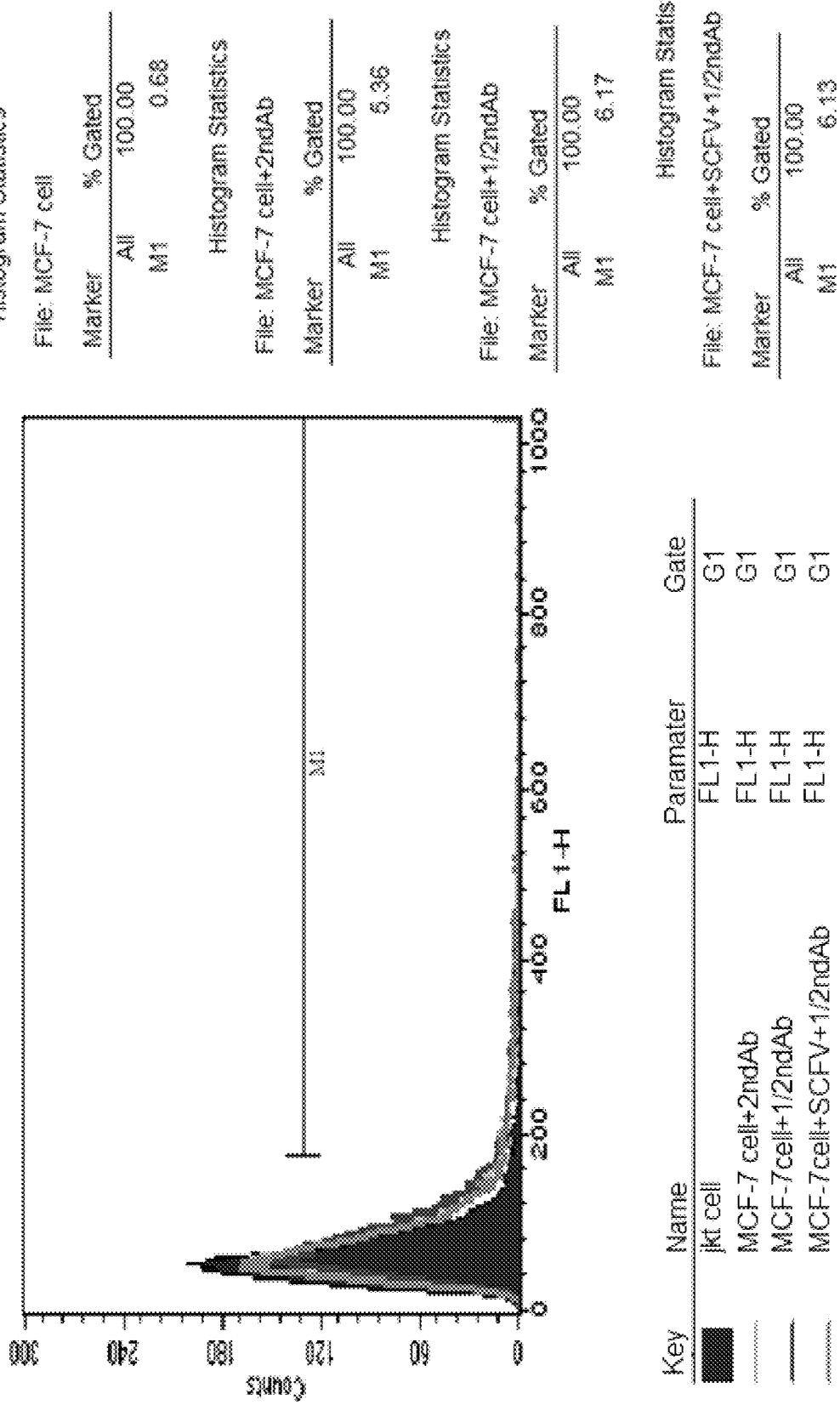

The ability of the antibody to activate purified killer CD8+ T cells co-cultured with MCF-7 and MDA-231 cell lines was evaluated using a LDH release cytotoxicity assay supplied by Cayman Labs per the manufacturer's instructions at different concentrations. Flow cytometry based binding assays were also performed using a secondary anti-His antibody to quantify the binding activity of the 83D4 BITE antibody candidate. The results indicated that the 83D4 BITE antibody was not able to bind to target cells effectively using the flow cytometry assay (FIG. 2) nor activate the killer T cells to lyse the MCF-7 tumor cells (Table 2). The antibody was also tested against a purified form of the TAG-72 immobilized within wells to see if it could recognize the TAG-72 target and this was negative as well (Table 1).

TABLE 1

83D4 binding to purified TAG-72 target was negative.

| Coating | Sample | A490 |
|---|---|---|
| Ag-1, 0.05 µg/100 µl/well | TGE Supernatant of 83sf-OKT3 | 0.077 |
| Ag-1, 0.05 µg/100 µl/well | Medium(DMEM + 10% FCS) | 0.072 |
| Ag-1, 0.05 µg/100 µl/well | PBS | 0.072 |
| Ag-2, 0.05 µg/100 µl/well | TGE Supernatant of 83sf-OKT3 | 0.073 |
| Ag-2, 0.05 µg/100 µl/well | Medium(DMEM + 10% FCS) | 0.071 |
| Ag-2, 0.05 µg/100 µl/well | PBS | 0.073 |
| Ag-1, 0.5 µg/100 µl/well | TGE Supernatant of 83sf-OKT3 | 0.071 |
| Ag-1, 0.5 µg/100 µl/well | Medium(DMEM + 10% FCS) | 0.070 |
| Ag-1, 0.5 µg/100 µl/well | PBS | 0.069 |
| Ag-2, 0.5 µg/100 µl/well | TGE Supernatant of 83sf-OKT3 | 0.070 |
| Ag-2, 0.5 µg/100 µl/well | Medium(DMEM + 10% FCS) | 0.071 |
| Ag-2, 0.5 µg/100 µl/well | PBS | 0.069 |
| Ag-1, 1 µg/100 µl/well | TGE Supernatant of 83sf-OKT3 | 0.075 |
| Ag-1, 1 µg/100 µl/well | Medium(DMEM + 10% FCS) | 0.072 |
| Ag-1, 1 µg/100 µl/well | PBS | 0.073 |
| Ag-2, 1 µg/100 µl/well | TGE Supernatant of 83sf-OKT3 | 0.071 |
| Ag-2, 1 µg/100 µl/well | Medium(DMEM + 10% FCS) | 0.072 |
| Ag-2, 1 µg/100 µl/well | PBS | 0.072 |
| control protein with His Tag, 1 µg/100 µl/well | PBS | 1.449 |

TABLE 2

LDH release assay for MCF-7 cells showing no increase in LDH levels when antibody was added

| Sample | Concentration (mU/mL) |
|---|---|
| Media | 0.46 |
| Ab | 0.52 |
| PBMC | 0.50 |
| MCF7 | 1.08 |
| MCF7 + Ab | 1.03 |
| MCF7 + PBMC | 0.96 |
| MCF7 + PBMC + Ab (no wash) | 0.96 |
| MCF7 + PBMC + AB (wash) | 0.93 |

Figure 3:
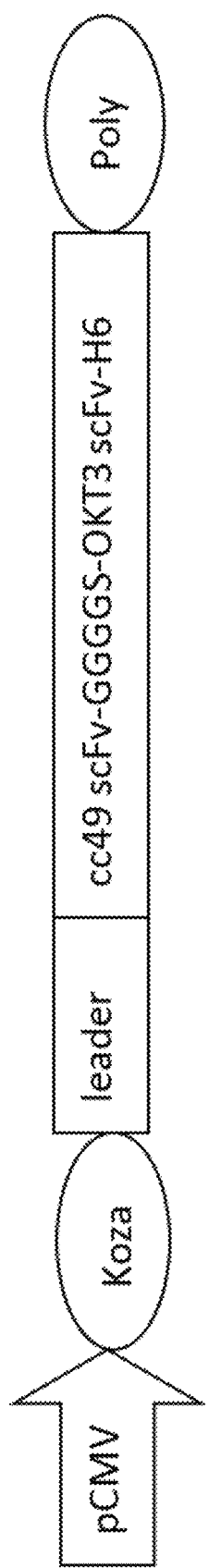
FIG. 3 is a map of the CC49 expression cassette. GGGGS is SEQ ID NO: 18.

The conclusion from these experiments using the 83D4 BITE was that this would not be a good candidate to study due to little binding to the target. This issue is likely due to the fact that when taking a naturally produced antibody such as the 83D4, there is a significant chance that its binding activity will be altered when synthetically produced in a tandem BITE antibody format. This is part of the difficulty inherent in developing these types of therapies. Therefore, another TAG-72 clone was selected termed CC49 which had been used successfully in other antibody formats and binds TAG-72 with good affinity. The CC49 sequence was used to prepare an engineered plasmid (FIG. 3).

The CC49 antibody exhibited different binding properties when compared to the initial 83D4 candidate. The initial testing of binding to TAG-72 purified target determined that CC49 did indeed recognize and bind the TAG-72 target with higher affinity (Table 3).

TABLE 3

ELISA binding of CC49 to purified TAG-72 target was positive in this case compared to negative controls.

| | OD490 | | | |
|---|---|---|---|---|
| Items | Coating: Mucin($H_2O$) | | Coating: Mucin(HCl) | |
| CC49-2/BITE | 0.308 | 0.310 | 0.364 | 0.366 |
| Medium | 0.079 | 0.077 | 0.086 | 0.088 |
| PBS | 0.079 | 0.074 | 0.083 | 0.084 |

Figure 4A:
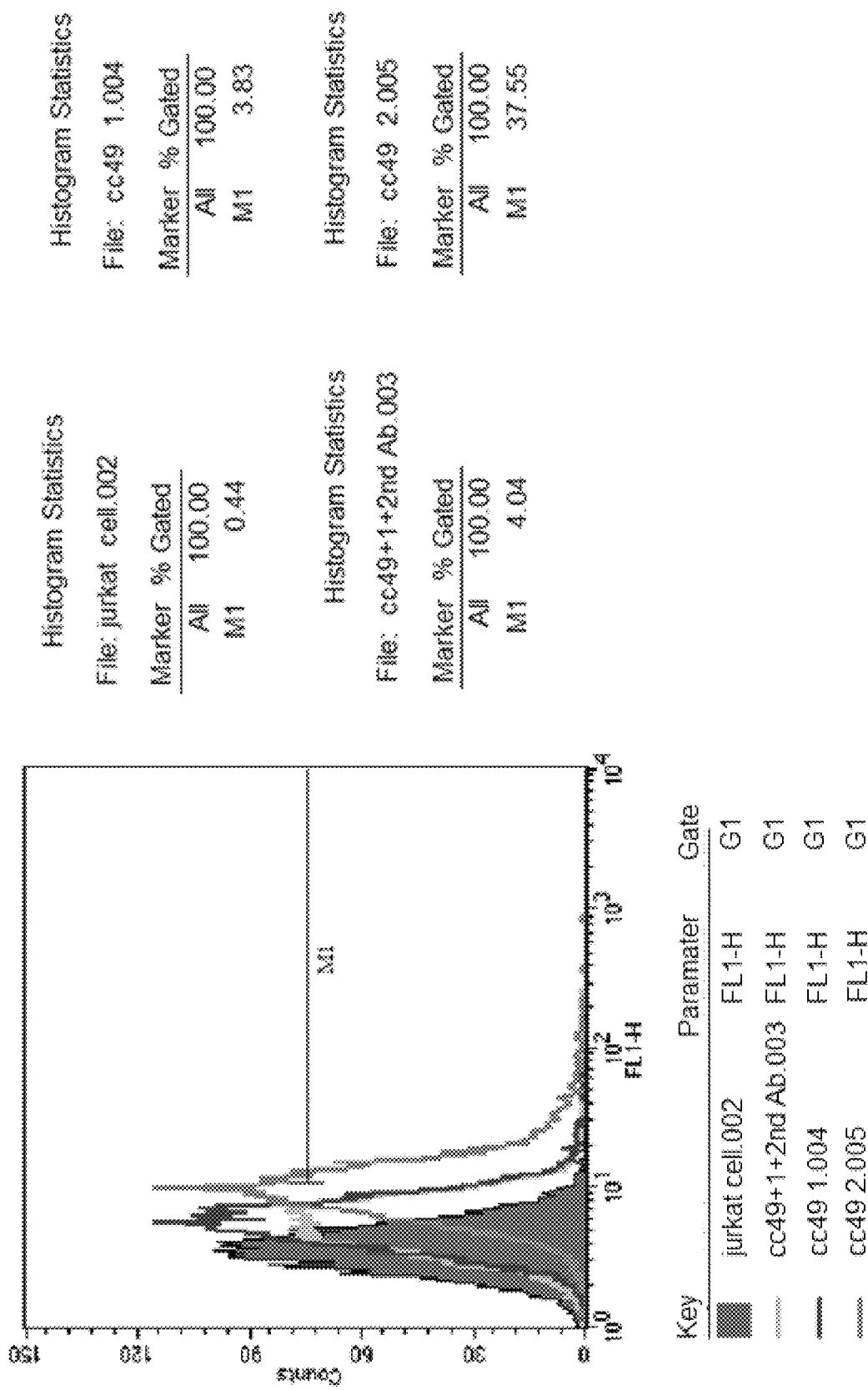
FIGS. 4A and 4B shows flow cytometry binding of CC49 antibody to jurkat (FIG. 4A) and MCF-7 (FIG. 4B) cell lines.

Note that the construct with the VH-linker-VL sequence (CC49-1) failed to recognize Jurkat cells (a transformed T cell line that expresses CD3) (FIG. 4A). However, the second construct (CC49-2) with the reverse sequence VL-linker-VH does bind to the Jurkat cells indicating that it can recognize the cells (FIG. 4A).

Figure 4B:
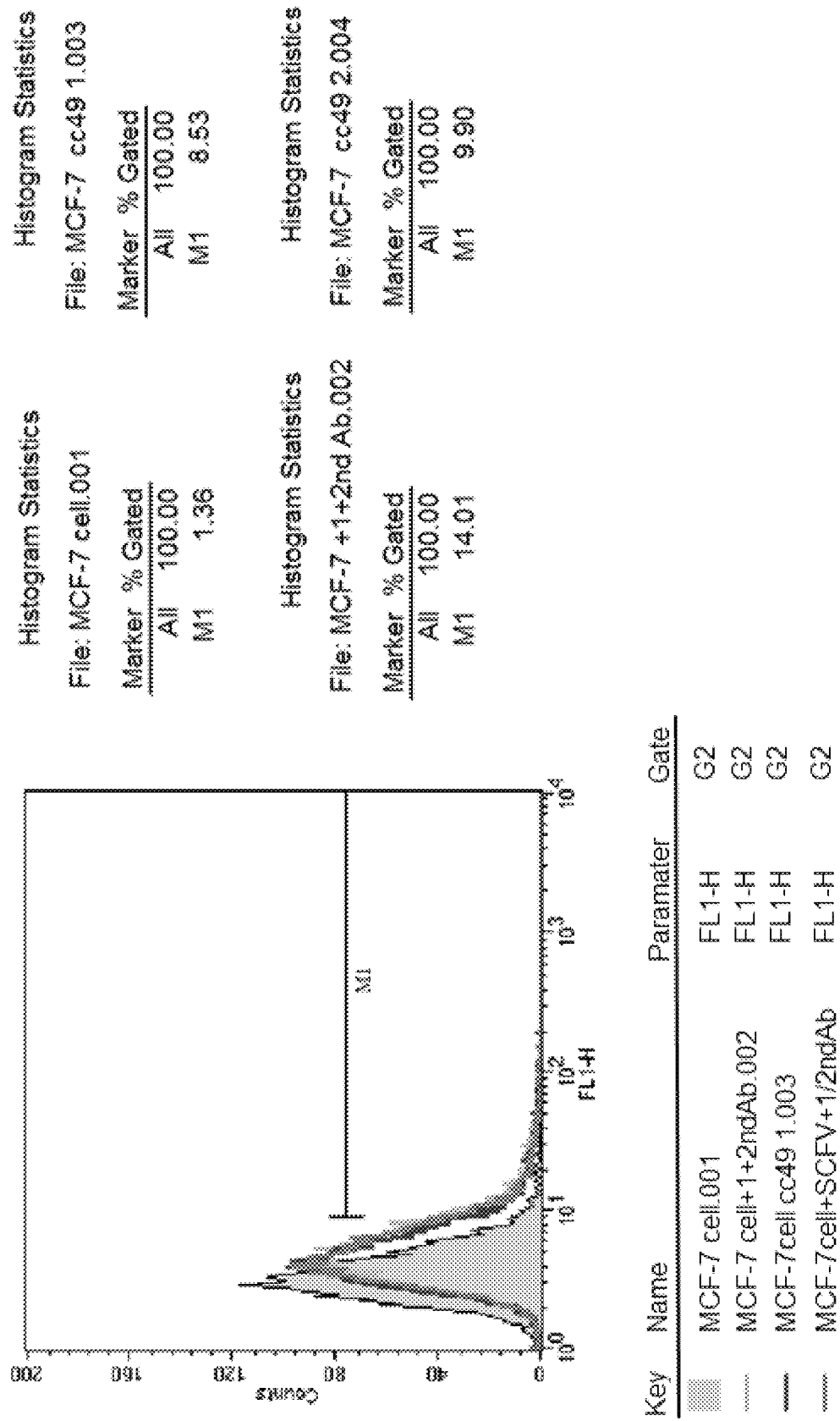

The binding of CC49 was checked in the MCF-7 cells as well using a flow cytometry assay. This data did show improved binding to the MCF-7 when compared to the 83D4 but was still relatively weak (FIG. 4B).

Figure 5B:
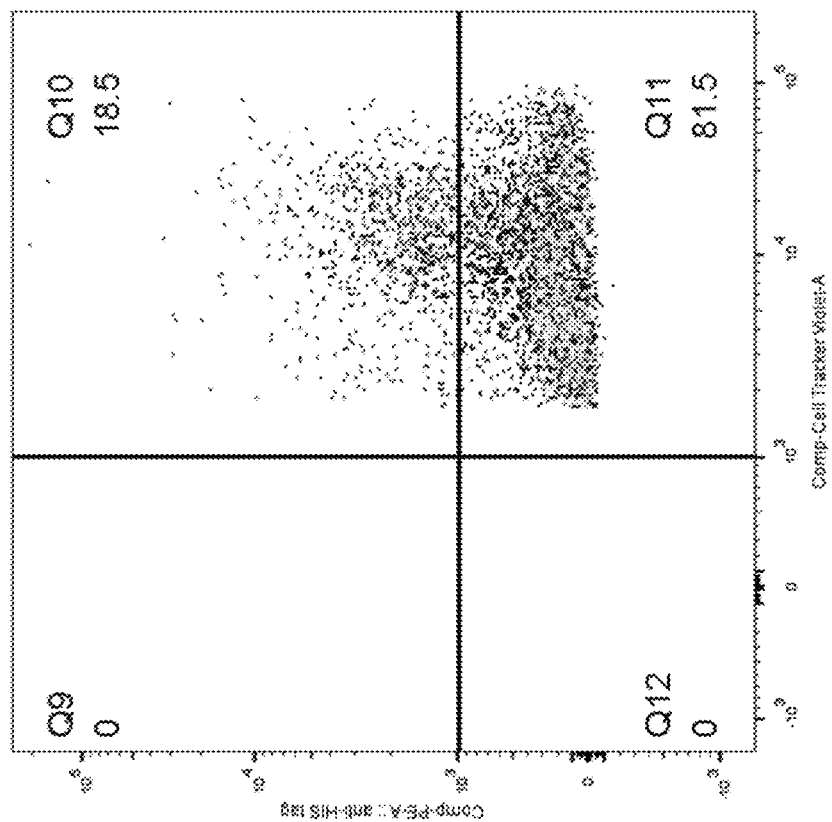
FIGS. 5A and 5B show dose dependent binding of CC49 antibody to MCF-7 cells using 200 μg (FIG. 5A, 9.89% binding) and 400 μg (FIG. 5B, 18.5% binding) antibody.
Figure 5A:
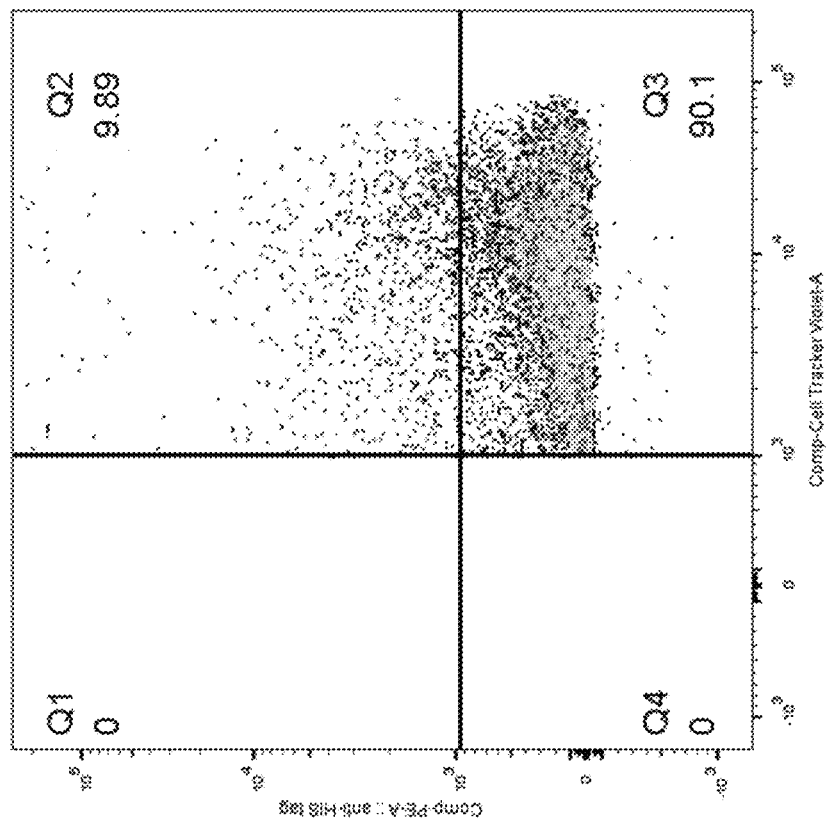
Figure 6:
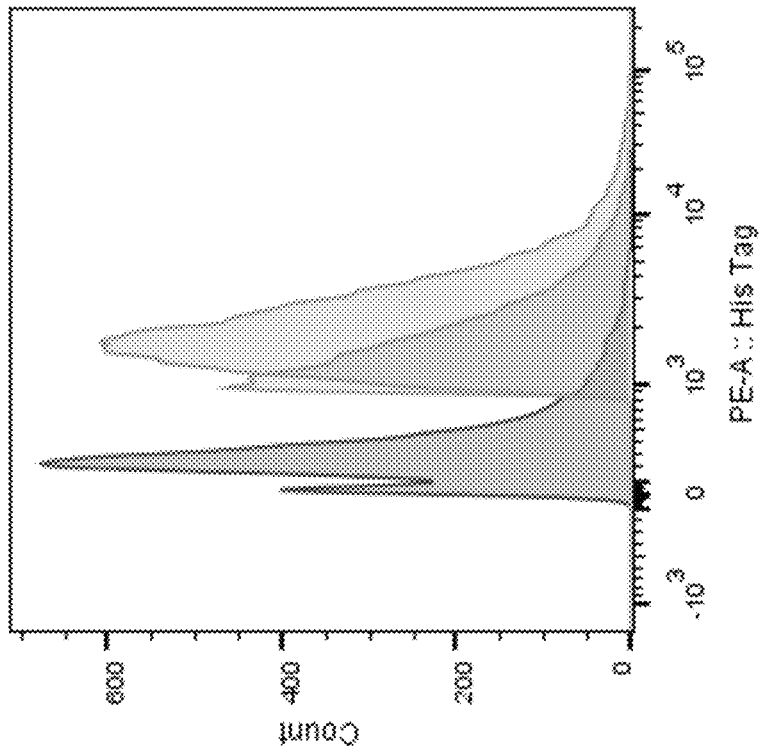
FIG. 6 shows TAG-72 BITE binding to OVACAR3.
Figure 7:
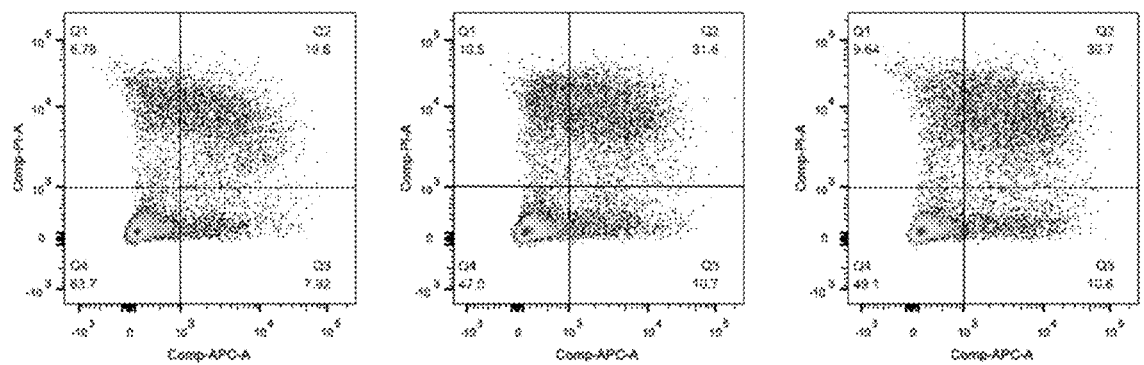
FIG. 7 shows T cell mediated killing by TAG-72 BITE.

The decision was made to also interrogate the antibody on other cell lines which were known to have a higher fraction of the TAG-72 target that is specifically bound by the CC49 antibody. This is because it is known that there are some differences in the TAG-72 glycoprotein between different cell lines and some antibodies may recognize one version better than another. The 83D4 antibody was initially used to bind to MCF-7 cells but a review of the literature suggested that CC49 could bind certain ovarian cancer cell lines well such as OVACAR-3. There is a dose dependent increase in the percentage of cells bound by the antibody as it is increased from 200 µg to 400 µg (from 9.89% to 18.5%, FIG. 5). OVACAR3 target cells that express TAG-72 are bound by TAG-72 BITE under proper culture conditions (FIG. 6), and there is evidence of T cell activation (FIG. 7).

The pilot project was successful in producing a candidate BITE antibody (CC49-OKT3) that can bind the TAG-72 purified target and also bind in a dose dependent manner to a cancer cell line OVACAR-3.

Example 2: TAG-72 T Cell Engager Antibody

Effective redirected T cell killing is accomplished using a T cell engager antibody against TAG-72 expressed on the surface of breast and ovarian cancer cells. Demonstrated is specific binding to the target in these tissues when the target is expressed, trafficking of T cells to the malignant cells, activated T cell mediated killing in vitro, and good biodistribution of the antibody in a mouse model with a human xenograft+/−infused human T cells to show trafficking of the T cells to the tumor in vivo.

In vitro testing and characterization of CC49-CD3 TAG-72 is done to determine optimal relative potency and specificity against various cancer cell lines (i.e. BT-474, MCF-7, OVACAR-3) in 3D spheroid tumor tissue culture systems with naïve T cells added in.

Pharmacokinetics and biodistribution data is generated in tumor bearing NSG mice.

Initial in vivo efficacy testing of the CC49-CD3 TAG-72 antibody in NSG mice with MCF-7 xenograft tumors with injected human CD8+ T cells is done to show immune activation and growth inhibition.

Complementary in vivo testing of the CC49-CD3 in CD34+ humanized NSG with xenografts is done to study immune trafficking in xenografts with and without antibody as well as examination of antibody immunogenicity.

This involves first complete in vitro testing of current CC49 TAG-72 on MCF7, MCF-7 DOX, MB231, OVACAR3 cell line spheroids. Next, sialyltransferase 7A knockout MCF-7 cell lines are generated via CRISPER/Cas9 double nickase kits and negative control is characterized by flow and western. Additional CC49 antibody and control 83D4 nonbinding BITE are produced in preparation for initial mouse experiments (estimated at 20 mg subject to change based on BD/PK studies). Finally, IND supporting studies are done to determine animal models for immunoreactivity, safety, PK, etc. and human tissues for binding specificity.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 19
SEQ ID NO: 1              moltype = DNA   length = 345
FEATURE                   Location/Qualifiers
misc_feature              1..345
                          note = synthetic construct
source                    1..345
                          mol_type = other DNA
                          organism = synthetic construct
SEQUENCE: 1
caggttcagt tgcagcagtc tgacgctgag ttggtgaaac ctggggcttc agtgaagatt  60
tcctgcaagg cttctggcta caccttcact gaccatgcaa ttcactgggt gaaacagaac 120
cctgaacagg gcctggaatg gattggatat ttttctcccg gaaatgatga ttttaaatac 180
aatgagaggt tcaagggcaa ggccacactg actcagaca aatcctccag cactgcctac 240
gtgcagctca acagcctgac atctgaggat tctgcagtgt atttctgtac aagatccctg 300
aatatggcct actggggtca aggaacctca gtcaccgtct cctca              345

SEQ ID NO: 2              moltype = AA   length = 115
FEATURE                   Location/Qualifiers
REGION                    1..115
                          note = synthetic construct
source                    1..115
                          mol_type = protein
                          organism = synthetic construct
SEQUENCE: 2
QVQLQQSDAE LVKPGASVKI SCKASGYTFT DHAIHWVKQN PEQGLEWIGY FSPGNDDFKY  60
NERFKGKATL TADKSSSTAY VQLNSLTSED SAVYFCTRSL NMAYWGQGTS VTVSS      115

SEQ ID NO: 3              moltype = DNA   length = 339
FEATURE                   Location/Qualifiers
misc_feature              1..339
                          note = synthetic construct
source                    1..339
                          mol_type = other DNA
                          organism = synthetic construct
SEQUENCE: 3
gacattgtga tgtcacagtc tccatcctcc ctacctgtgt cagttggcga gaaggttact  60
ttgagctgca agtccagtca gagccttta tatagtggta atcaaaagaa ctacttggcc 120
tggtaccagc agaaaccagg gcagtctcct aaactgctga tttactgggc atccgctagg 180
gaatctgggg tccctgatcg cttcacaggc agtggatctg ggacagattt cactctctcc 240
atcagcagtg tgaagactga agacctggca gtttattact gtcagcagta ttatagctat 300
cccctcacgt tcggtgctgg gaccaagctg gtgctgaaa                        339

SEQ ID NO: 4              moltype = AA   length = 113
FEATURE                   Location/Qualifiers
REGION                    1..113
                          note = synthetic construct
source                    1..113
                          mol_type = protein
                          organism = synthetic construct
SEQUENCE: 4
DIVMSQSPSS LPVSVGEKVT LSCKSSQSLL YSGNQKNYLA WYQQKPGQSP KLLIYWASAR  60
ESGVPDRFTG SGSGTDFTLS ISSVKTEDLA VYYCQQYYSY PLTFGAGTKL VLK        113

SEQ ID NO: 5              moltype = AA   length = 25
FEATURE                   Location/Qualifiers
REGION                    1..25
                          note = synthetic construct
source                    1..25
                          mol_type = protein
                          organism = synthetic construct
```

-continued

```
SEQUENCE: 5
LSADDAKKDA AKKDDAKKDD AKKDL                                            25

SEQ ID NO: 6              moltype = AA  length = 253
FEATURE                   Location/Qualifiers
REGION                    1..253
                          note = synthetic construct
source                    1..253
                          mol_type = protein
                          organism = synthetic construct
SEQUENCE: 6
QVQLQQSDAE LVKPGASVKI SCKASGYTFT DHAIHWVKQN PEQGLEWIGY FSPGNDDFKY       60
NERFKGKATL TADKSSSTAY VQLNSLTSED SAVYFCTRSL NMAYWGQGTS VTVSSLSADD      120
AKKDAAKKDD AKKDDAKKDL DIVMSQSPSS LPVSVGEKVT LSCKSSQSLL YSGNQKNYLA      180
WYQQKPGQSP KLLIYWASAR ESGVPDRFTG SGSGTDFTLS ISSVKTEDLA VYYCQQYYSY      240
PLTFGAGTKL VLK                                                        253

SEQ ID NO: 7              moltype = AA  length = 253
FEATURE                   Location/Qualifiers
REGION                    1..253
                          note = synthetic construct
source                    1..253
                          mol_type = protein
                          organism = synthetic construct
SEQUENCE: 7
DIVMSQSPSS LPVSVGEKVT LSCKSSQSLL YSGNQKNYLA WYQQKPGQSP KLLIYWASAR       60
ESGVPDRFTG SGSGTDFTLS ISSVKTEDLA VYYCQQYYSY PLTFGAGTKL VLKLSADDAK      120
KDAAKKDDAK KDDAKKDLQV QLQQSDAELV KPGASVKISC KASGYTFTDH AIHWVKQNPE      180
QGLEWIGYFS PGNDDFKYNE RFKGKATLTA DKSSSTAYVQ LNSLTSEDSA VYFCTRSLNM      240
AYWGQGTSVT VSS                                                        253

SEQ ID NO: 8              moltype = DNA  length = 762
FEATURE                   Location/Qualifiers
misc_feature              1..762
                          note = synthetic construct
source                    1..762
                          mol_type = other DNA
                          organism = synthetic construct
SEQUENCE: 8
gggggggggg gatccgatat caaactgcag cagagcggag ccgaactggc aagacccgga       60
gcaagcgtca aaatgtcatg taaaacctca gggtacacat tcactaggta taccatgcac     120
tgggtgaaac agcgaccagg acagggtctg gagtggatcg atatattaa ccctcccga      180
gggtacacaa actacaacca gaagtttaaa gacaaggcca cactgaccac cgataagtcc     240
agctctactg cttacatgca gctgagttca ctgaccagcg aggactctgc tgtgtactat     300
tgcgcaaggt actatgacga tcattactgt ctggattatt ggggccaggg aactaccctg     360
actgtgtcca gcgtcgaagg cggaagtggg ggttcaggcg gaagcggggg ttctggcgga     420
gtcgacgata tccagctgac ccagagcccc gcaattatgt cctctaagtc tggcgaaaaa     480
gtgaccatga catgcagagc ctctagttca gtctcctaca tgaattggta tcagcagaaa     540
agtggaacaa gccctaagag atggatctac gacacttcta aggtggcatc cggcgtccca     600
tatcgcttca gcgggtctgg tagtggcact tcatactccc tgaccatttc cagcatggag     660
gctgaagatg ccgctacata ctattgtcag cagtggtcta gtaaccctct gacctttggg     720
gctgaactaa aactggaact gaagcatcat catcatcatc ac                        762

SEQ ID NO: 9              moltype = AA  length = 254
FEATURE                   Location/Qualifiers
REGION                    1..254
                          note = synthetic construct
source                    1..254
                          mol_type = protein
                          organism = synthetic construct
SEQUENCE: 9
GGGGSDIKLQ QSGAELARPG ASVKMSCKTS GYTFTRYTMH WVKQRPGQGL EWIGYINPSR       60
GYTNYNQKFK DKATLTTDKS SSTAYMQLSS LTSEDSAVYY CARYYDDHYC LDYWGQGTTL      120
TVSSVEGGSG GSGGSGGSGG VDDIQLTQSP AIMSASPGEK VTMTCRASSS VSYMNWYQQK      180
SGTSPKRWIY DTSKVASGVP YRFSGSGSGT SYSLTISSME AEDAATYYCQ QWSSNPLTFG      240
AGTKLELKHH HHHH                                                       254

SEQ ID NO: 10             moltype = AA  length = 507
FEATURE                   Location/Qualifiers
REGION                    1..507
                          note = synthetic construct
source                    1..507
                          mol_type = protein
                          organism = synthetic construct
SEQUENCE: 10
QVQLQQSDAE LVKPGASVKI SCKASGYTFT DHAIHWVKQN PEQGLEWIGY FSPGNDDFKY       60
NERFKGKATL TADKSSSTAY VQLNSLTSED SAVYFCTRSL NMAYWGQGTS VTVSSLSADD      120
AKKDAAKKDD AKKDDAKKDL DIVMSQSPSS LPVSVGEKVT LSCKSSQSLL YSGNQKNYLA      180
WYQQKPGQSP KLLIYWASAR ESGVPDRFTG SGSGTDFTLS ISSVKTEDLA VYYCQQYYSY      240
```

```
PLTFGAGTKL VLKGGGGSDI KLQQSGAELA RPGASVKMSC KTSGYTFTRY TMHWVKQRPG    300
QGLEWIGYIN PSRGYTNYNQ KFKDKATLTT DKSSSTAYMQ LSSLTSEDSA VYYCARYYDD    360
HYCLDYWGQG TTLTVSSVEG GSGGGGGSGG SGGVDDIQLT QSPAIMSASP GEKVTMTCRA    420
SSSVSYMNWY QQKSGTSPKR WIYDTSKVAS GVPYRFSGSG SGTSYSLTIS SMEAEDAATY    480
YCQQWSSNPL TFGAGTKLEL KHHHHHH                                       507

SEQ ID NO: 11           moltype = AA   length = 507
FEATURE                 Location/Qualifiers
REGION                  1..507
                        note = synthetic construct
source                  1..507
                        mol_type = protein
                        organism = synthetic construct
SEQUENCE: 11
DIVMSQSPSS LPVSVGEKVT LSCKSSQSLL YSGNQKNYLA WYQQKPGQSP KLLIYWASAR     60
ESGVPDRFTG SGSGTDFTLS ISSVKTEDLA VYYCQQYYSY PLTFGAGTKL VLKLSADDAK    120
KDAAKKDDAK KDDAKKDLQV QLQQSDAELV KPGASVKISC KASGYTFTDH AIHWVKQNPE    180
QGLEWIGYFS PGNDDFKYNE RFKGKATLTA DKSSSTAYVQ LNSLTSEDSA VYFCTRSLNM    240
AYWGQGTSVT VSSGGGGSDI KLQQSGAELA RPGASVKMSC KTSGYTFTRY TMHWVKQRPG    300
QGLEWIGYIN PSRGYTNYNQ KFKDKATLTT DKSSSTAYMQ LSSLTSEDSA VYYCARYYDD    360
HYCLDYWGQG TTLTVSSVEG GSGGSGGSGG SGGVDDIQLT QSPAIMSASP GEKVTMTCRA    420
SSSVSYMNWY QQKSGTSPKR WIYDTSKVAS GVPYRFSGSG SGTSYSLTIS SMEAEDAATY    480
YCQQWSSNPL TFGAGTKLEL KHHHHHH                                       507

SEQ ID NO: 12           moltype = AA   length = 5
FEATURE                 Location/Qualifiers
REGION                  1..5
                        note = synthetic construct
source                  1..5
                        mol_type = protein
                        organism = synthetic construct
SEQUENCE: 12
DHAIH                                                                 5

SEQ ID NO: 13           moltype = AA   length = 20
FEATURE                 Location/Qualifiers
REGION                  1..20
                        note = synthetic construct
source                  1..20
                        mol_type = protein
                        organism = synthetic construct
SEQUENCE: 13
WIGYFSPGND DFKYNERFKG                                                20

SEQ ID NO: 14           moltype = AA   length = 5
FEATURE                 Location/Qualifiers
REGION                  1..5
                        note = synthetic construct
source                  1..5
                        mol_type = protein
                        organism = synthetic construct
SEQUENCE: 14
LNMAY                                                                 5

SEQ ID NO: 15           moltype = AA   length = 17
FEATURE                 Location/Qualifiers
REGION                  1..17
                        note = synthetic construct
source                  1..17
                        mol_type = protein
                        organism = synthetic construct
SEQUENCE: 15
KSSQSLLYSG NQKNYLA                                                   17

SEQ ID NO: 16           moltype = AA   length = 7
FEATURE                 Location/Qualifiers
REGION                  1..7
                        note = synthetic construct
source                  1..7
                        mol_type = protein
                        organism = synthetic construct
SEQUENCE: 16
WASARES                                                               7

SEQ ID NO: 17           moltype = AA   length = 9
FEATURE                 Location/Qualifiers
REGION                  1..9
                        note = synthetic construct
source                  1..9
```

```
                        mol_type = protein
                        organism = synthetic construct
SEQUENCE: 17
QQYYSYPLT                                                             9

SEQ ID NO: 18           moltype = AA  length = 5
FEATURE                 Location/Qualifiers
REGION                  1..5
                        note = synthetic construct
source                  1..5
                        mol_type = protein
                        organism = synthetic construct
SEQUENCE: 18
GGGGS                                                                 5

SEQ ID NO: 19           moltype = AA  length = 249
FEATURE                 Location/Qualifiers
REGION                  1..249
                        note = synthetic construct
source                  1..249
                        mol_type = protein
                        organism = synthetic construct
SEQUENCE: 19
DIKLQQSGAE LARPGASVKM SCKTSGYTFT RYTMHWVKQR PGQGLEWIGY INPSRGYTNY    60
NQKFKDKATL TTDKSSSTAY MQLSSLTSED SAVYYCARYY DDHYCLDYWG QGTTLTVSSV   120
EGGSGGSGGS GGSGGVDDIQ LTQSPAIMSA SPGEKVTMTC RASSSVSYMN WYQQKSGTSP   180
KRWIYDTSKV ASGVPYRFSG SGSGTSYSLT ISSMEAEDAA TYYCQQWSSN PLTFGAGTKL   240
ELKHHHHHH                                                          249
```

What is claimed is:

1. A bispecific antibody, comprising
an anti-TAG72 single chain variable fragment (scFv) antibody that specifically binds human TAG72 linked to an anti-CD3 scFv that specifically binds human CD3 epsilon subunit,
wherein the anti-TAG72 scFv comprises a variable heavy ($V_H$) domain and a variable light ($V_L$) domain separated by a peptide linker,
wherein the $V_H$ domain comprises CDR1, CDR2 and CDR3 domains having the amino acid sequences of SEQ ID NOs: 12, 13 and 14, respectively, and
wherein the $V_L$ domain comprises CDR1, CDR2 and CDR3 domains having the amino acid sequences of SEQ ID NOs: 15, 16 and 17, respectively.

2. The bispecific antibody of claim 1, wherein the anti-TAG72 $V_H$ domain comprises the amino acid sequence of SEQ ID NO: 2.

3. The bispecific antibody of claim 1, wherein the anti-TAG72 $V_L$ domain comprises the amino acid sequence of SEQ ID NO:4.

4. The bispecific antibody of claim 1, wherein the anti-CD3 scFv comprises the amino acid sequence of SEQ ID NO:19.

5. The bispecific antibody of claim 1, wherein the antibody comprises the amino acid sequence of SEQ ID NO: 11.

6. A pharmaceutical composition, comprising the bispecific antibody of claim 1 in a pharmaceutically acceptable carrier.

* * * * *